(12) United States Patent
Chang et al.

(10) Patent No.: US 11,083,893 B2
(45) Date of Patent: Aug. 10, 2021

(54) ELECTRICAL STIMULATION DEVICE, METHOD FOR GENERATING ELECTRICAL SIGNALS, AND COMPUTER-READABLE MEDIUM

(71) Applicant: GIMER MEDICAL. Co. LTD., New Taipei (TW)

(72) Inventors: Chi-Heng Chang, New Taipei (TW); Jian-Hao Pan, New Taipei (TW)

(73) Assignee: GIMER MEDICAL. CO. LTD., New Taipei (TW)

( * ) Notice: Subject to any disclaimer, the term of this patent is extended or adjusted under 35 U.S.C. 154(b) by 151 days.

(21) Appl. No.: 16/107,359

(22) Filed: Aug. 21, 2018

(65) Prior Publication Data

US 2019/0060651 A1 Feb. 28, 2019

(30) Foreign Application Priority Data

Aug. 22, 2017 (CN) .......................... 201710722664.2

(51) Int. Cl.
*A61N 1/36* (2006.01)
*A61N 1/05* (2006.01)
*A61N 1/378* (2006.01)

(52) U.S. Cl.
CPC ....... *A61N 1/36062* (2017.08); *A61N 1/0551* (2013.01); *A61N 1/36071* (2013.01);
(Continued)

(58) Field of Classification Search
CPC .. A61N 1/36; A61N 1/36017; A61N 1/36021; A61N 1/3603; A61N 1/3605;
(Continued)

(56) References Cited

U.S. PATENT DOCUMENTS 5,817,141 A * 10/1998 Iimori ...................... A61N 1/32
607/76
9,037,255 B2 * 5/2015 Rocke ................ A61N 1/36046
607/62
(Continued)

FOREIGN PATENT DOCUMENTS

| EP | 1501591 A1 | 2/2005 |
| EP | 3159038 A1 | 4/2017 |
| WO | WO 2005/002663 A2 | 1/2005 |

OTHER PUBLICATIONS

Extended European Search Report, dated Jan. 30, 2019 in corresponding European Application No. 18188979.1.
(Continued)

*Primary Examiner* — Ahmed M Farah
(74) *Attorney, Agent, or Firm* — Birch, Stewart, Kolasch & Birch, LLP

(57) ABSTRACT

An electrical stimulation device is provided. The electrical stimulation device includes a power management circuit and an electrical stimulation generation circuit. The power management circuit generates a first voltage and a second voltage to power the electrical stimulation generation circuit. The electrical stimulation generation circuit includes a working-electrode contact and a reference-electrode contact. The electrical stimulation generation circuit generates a first electrical signal at the working-electrode contact and further generates a second electrical signal at the reference-electrode contact. The first electrical signal comprises a plurality of first alternating-current (AC) pulses configuring to for electrically stimulate a target region of a target object.

9 Claims, 15 Drawing Sheets

(52) U.S. Cl.
CPC ......... *A61N 1/36125* (2013.01); *A61N 1/378* (2013.01); *A61N 1/36021* (2013.01)

(58) Field of Classification Search
CPC ............ A61N 1/36125; A61N 1/36128; A61N 1/378; A61N 1/00; A61N 1/04; A61N 1/05; A61N 1/0428; A61N 1/0502; A61N 1/0504; A61N 1/0507; A61N 1/0517; A61N 1/0519; A61N 1/0521; A61N 1/0526; A61N 1/0551
USPC ...... 607/2, 9, 72–76, 40, 41, 46, 66; 606/41, 606/42, 48, 80, 50
See application file for complete search history.

(56) References Cited

U.S. PATENT DOCUMENTS

| | | | | |
|---|---|---|---|---|
| 10,639,476 | B2* | 5/2020 | Chang | A61N 1/36071 |
| 2002/0022867 | A1* | 2/2002 | Akiyama | A61N 1/3937 |
| | | | | 607/66 |
| 2003/0212395 | A1* | 11/2003 | Woloszko | A61B 18/148 |
| | | | | 606/41 |
| 2004/0034394 | A1* | 2/2004 | Woods | A61N 1/37247 |
| | | | | 607/46 |
| 2004/0210289 | A1* | 10/2004 | Wang | B82Y 25/00 |
| | | | | 607/116 |
| 2004/0236391 | A1* | 11/2004 | Kobayashi | A61N 1/36034 |
| | | | | 607/72 |
| 2010/0070005 | A1* | 3/2010 | Rocke | A61N 1/36046 |
| | | | | 607/66 |
| 2017/0095667 | A1* | 4/2017 | Yakovlev | A61N 1/0553 |

OTHER PUBLICATIONS

Ultrasonic Power/Data Telemetry and Neural Stimulator With OOK-PM Signaling, published Dec. 1, 2013, IEEE Transactions on Circuits and Systems, II: Express Briefs, vol. 60, No. 12, Dec. 2013, pp. 827-831.

* cited by examiner

ELECTRICAL STIMULATION DEVICE, METHOD FOR GENERATING ELECTRICAL SIGNALS, AND COMPUTER-READABLE MEDIUM

CROSS REFERENCE TO RELATED APPLICATIONS

This Application claims priority of China Application No. 201710722664.2, filed on Aug. 22, 2017, the entirety of which is incorporated by reference herein.

BACKGROUND OF THE INVENTION

Field of the Invention

The invention relates to an electrical stimulation device, and more particularly to an implantable electrical stimulation device.

Description of the Related Art

Due to developments in precision manufacturing technology, medical instruments have been miniaturized and can be implanted in the human body. An example of this phenomenon is the implantable electrical stimulation device. Not only can implantable electrical stimulation devices be used to generate electrical stimulation to the spinal cord nerves to reduce patient's pain, but they can also be used to treat diseases by electrically stimulating specific nerves, such as bladder nerves and retinal nerves. However, as the nerves that may require electrical stimulation are in different locations in the human body, the electrical stimulation devices currently in use need to be configured with a more complicated switch array to select the corresponding electrodes and switch the positive/negative polarities of the electrodes. This increases the volume of the electrical stimulation devices and causes them to use more power. In addition to the positive and negative electrodes, in order to provide the appropriate level of reference voltage, the current electrical stimulation devices need to provide an additional reference electrode on a lead or on an extension.

BRIEF SUMMARY OF THE INVENTION

An exemplary embodiment of an electrical stimulation device is provided. The electrical stimulation device comprises a power management circuit and an electrical stimulation generation circuit. The power management circuit generates a first voltage and a second voltage to power the electrical stimulation generation circuit. The electrical stimulation generation circuit comprises a working-electrode contact and a reference-electrode contact. The electrical stimulation generation circuit generates a first electrical signal at the working-electrode contact and further generates a second electrical signal at the reference-electrode contact. The first electrical signal comprises a plurality of first alternating-current (AC) pulses configuring to for electrically stimulate a target region of a target object.

An exemplary embodiment of a method of generating electrical signals for an electrical stimulation device is provided. The electrical stimulation device comprises a power management circuit and an electrical stimulation generation circuit. The method comprises the steps of generating a first voltage and a second voltage by the power management circuit to power the electrical stimulation generation circuit; generating a first electrical signal at a working-electrode contact by the electrical stimulation generation circuit; and generating a second electrical signal at a reference-electrode contact by the electrical stimulation generation circuit. The first electrical signal comprises a plurality of first alternating-current (AC) pulses.

An exemplary embodiment of a computer-readable medium is provided. The computer-readable medium stores one or more instructions and operates with an electrical stimulation device which comprises a power management circuit and an electrical stimulation generation circuit. When the instructions are executed by the electrical stimulation device, the electrical stimulation device executes a plurality steps comprising: generating a first voltage and a second voltage to power the electrical stimulation generation circuit; generating a first electrical signal at a working-electrode contact of the electrical stimulation generation circuit; and generating a second electrical signal at a reference-electrode contact of the electrical stimulation generation circuit.

BRIEF DESCRIPTION OF THE DRAWINGS

The invention can be more fully understood by referring to the following detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
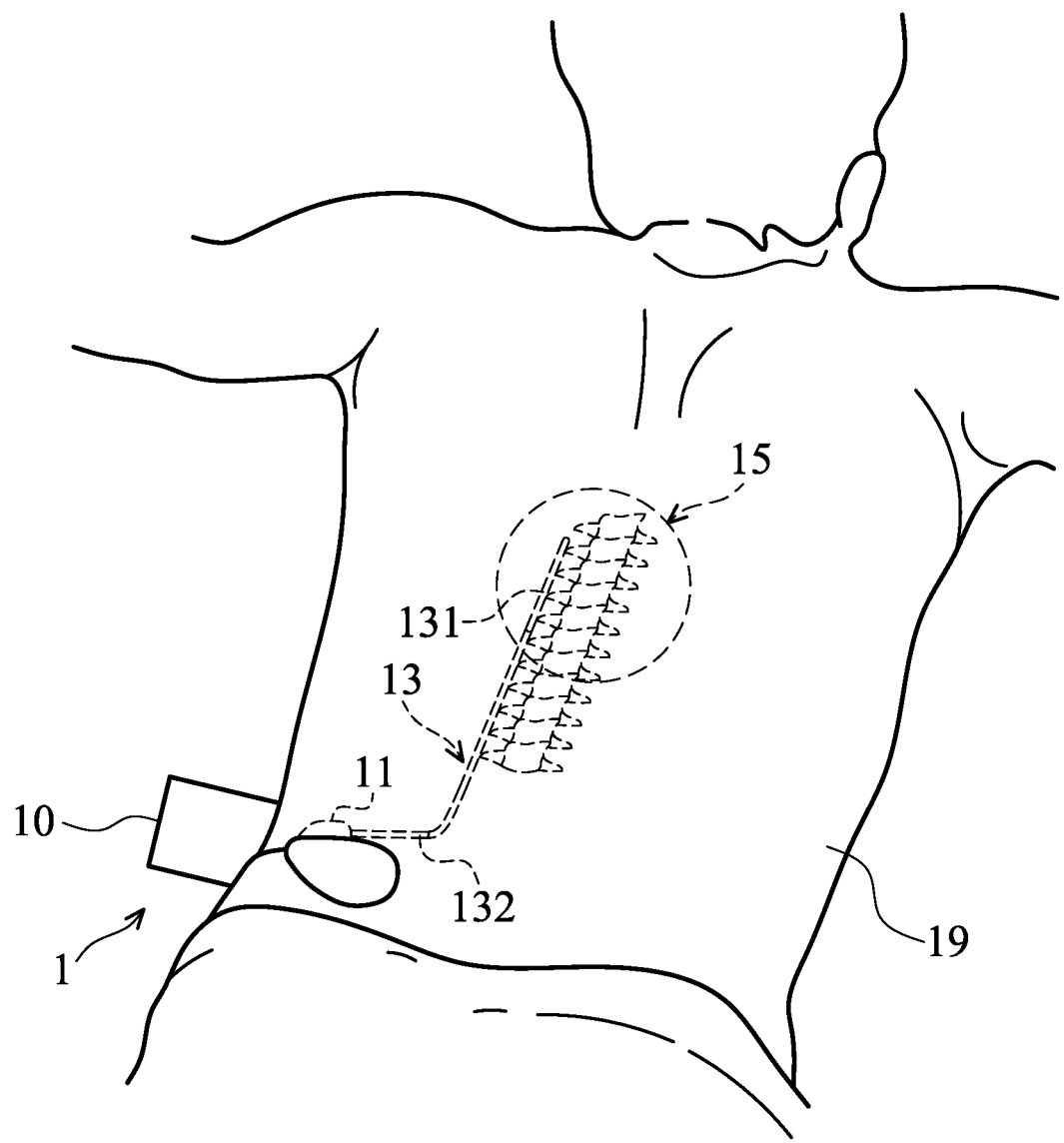
FIG. 1 shows an electrical stimulation system according to an exemplary embodiment of the present invention.

FIG. 1 shows an electrical stimulation system according to an exemplary embodiment of the present invention. Referring to FIG. 1, the electrical stimulation system 1 comprises an external control device 10, an electrical stimulation device 11, and a lead 13. The electrical stimulation device 11 comprises an electrical stimulation generation circuit (for example, an electrical stimulation generation circuit 110 shown in FIG. 5) and a power management circuit (for example, a power management circuit 111 shown in FIG. 5) which are disposed inside the housing. According to an embodiment of the present invention, the material of the housing may is plastic or a metal. In this embodiment, a plastic polymer material polyether polymer ketone (PEEK) is given as an example. The electrical stimulation device 11 is an implantable device which can be implanted in the interior of a target 19 (for example, a patient, which may be human or other mammalian). The lead 13 comprises a distal end 131 and a proximal end 132. The distal end 131 refers to the end of the lead 13 away from the electrical stimulation device 11, and the proximal end 132 is the end of the lead 13 close to the electrical stimulation device 11. When the lead 13 is placed near a specific region (or target region) within the target 19, the electrical stimulation generation circuit within the electrical stimulation device 11 transmits a plurality of electrical signals to a plurality electrodes on the distal end 131 through the lead 13 to electrically stimulate this specific region. For example, as shown in FIG. 1, the target 19 is a patient. When the electrical stimulation device 11 is implanted in the body of the patient 19, the electrical stimulation device 11 can be placed subcutaneously on the back of the patient 19, and the distal end 131 of the lead is placed in a specific region 15 close to the spinal cord nerve. For example, at least part of the distal end 131 of the lead is placed in the epidural space to electrically stimulate the spinal cord, spinal nerve, or a dorsal root ganglia (DRG) nearby. The electrical stimulation generation circuit in the electrical stimulation device 11 transmits the electrical signals through the lead 13 to the electrodes on the distal end 131 to electrically stimulate the target region. In addition, the target region that is electrically stimulated can also be in the brain for electrical stimulation of the brain cortex or deep brain stimulation (DBS).

Figure 2:
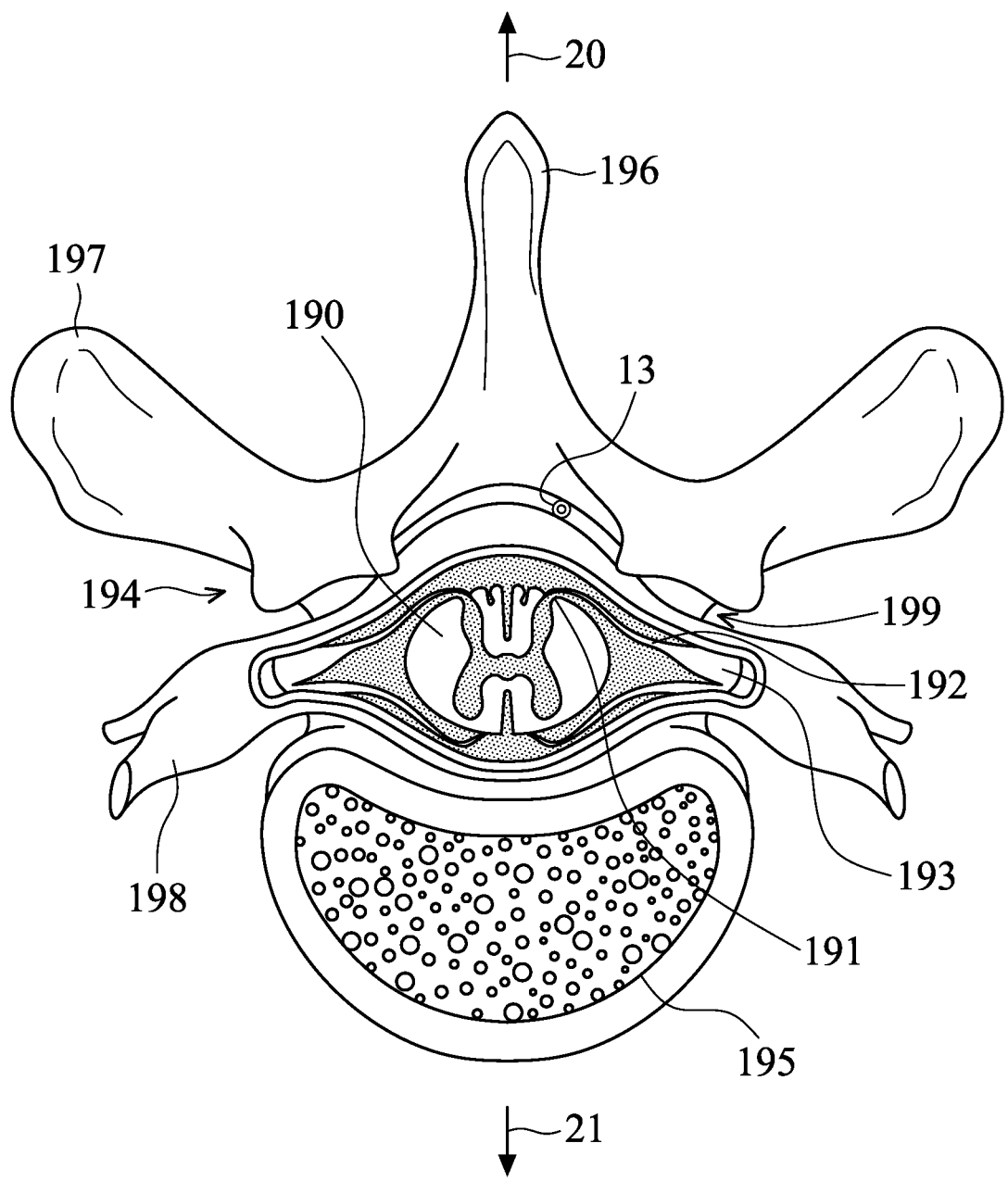
FIG. 2 is a schematic diagram showing a cross-sectional view of a vertebra.

FIG. 2 is an example of a cross-sectional view of a vertebra. This section shows major parts of the spine, such as the spinal cord and spinal cord nerves, including the dorsal root nerve entry zone 191, the dorsal root nerves 192, the dorsal root ganglions 193, the vertebra 194, the ventrally located vertebral body 195, the spinous process 196, the dorsally located transverse processes 197, the dura mater 198, and the epidural space 199. Referring to FIG. 2, for example, the vertebra 194 may be any section of the cervical vertebras, the thoracic vertebras, the lumbar vertebras, or the sacral vertebrae. In FIG. 2, the eighth thoracic vertebra (T8), the ninth thoracic vertebra (T9), or the tenth thoracic vertebra (T10) is given as an example. The arrow 20 shown in FIG. 2 indicates the direction of the back, and the arrow 21 indicates the direction of the abdomen. The spinal cord 190 is located between the ventrally located vertebral body 195, the dorsally located transverse processes 197, and the spinous process 196. The spinal cord 190 is located within the dura mater 198, which surrounds a portion of the nerves exiting the spinal cord (including the dorsal root nerves 192 and the dorsal root ganglions 193). According to an embodiment of the present invention, the distal end of lead 13 enters and approaches a specific region to be electrically stimulated through the epidural space 199.

Figure 3:
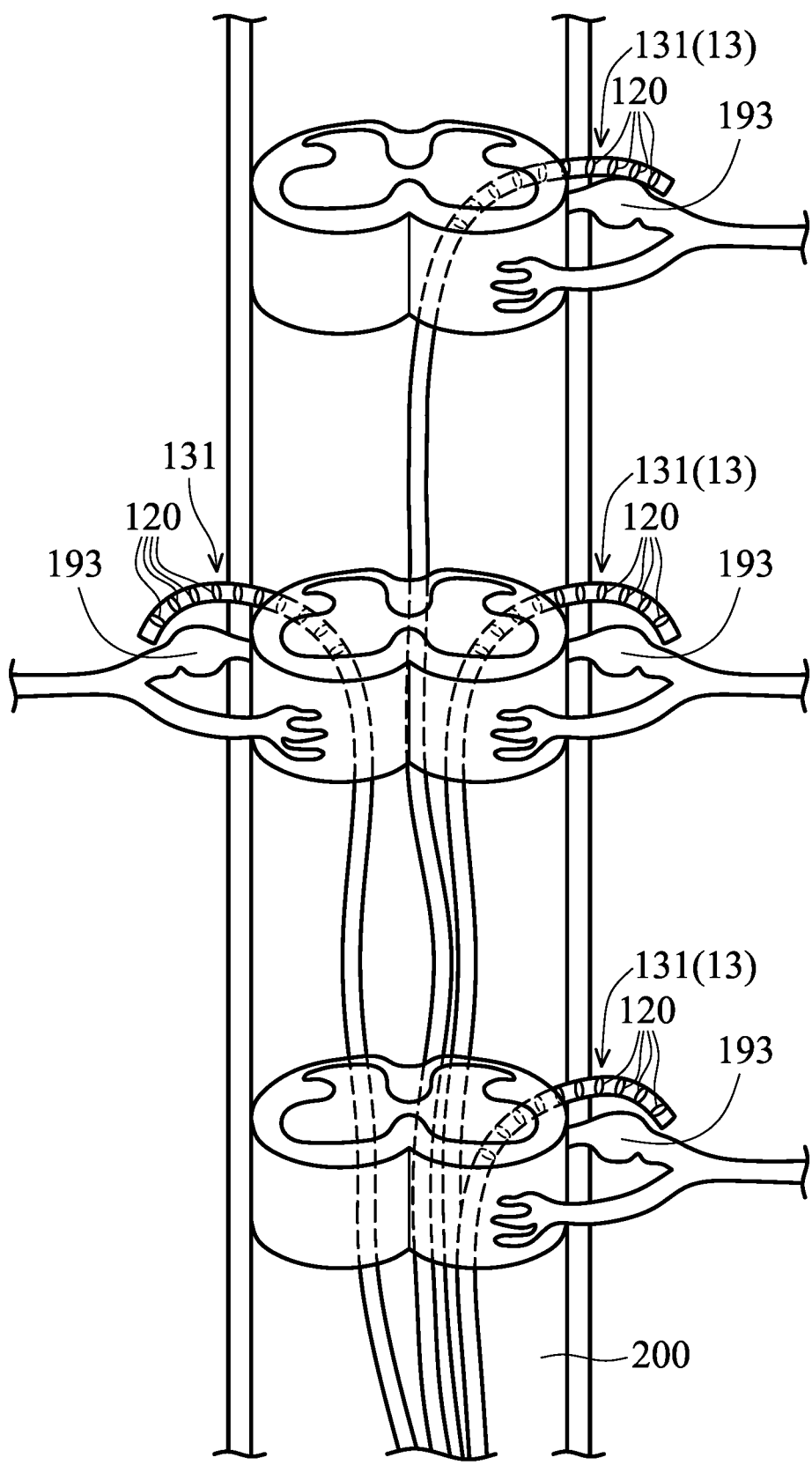
FIG. 3 is a schematic diagram showing the distal end of a lead placed near the dorsal root ganglion according to an embodiment of the present invention.

FIG. 3 is a schematic diagram showing the distal end 131 placed near the dorsal root ganglion according to an embodiment of the present invention. In FIG. 3 it is shown that the distal ends 131 of four leads 13 are positioned close to the dorsal root ganglions 193 at the different (vertebra) levels. The proximal end 132 of each lead 13 is connected to the electrical stimulation device 11 (as shown in FIG. 1), and a plurality of electrodes 120 are disposed on the distal end 131.

Figure 4A:
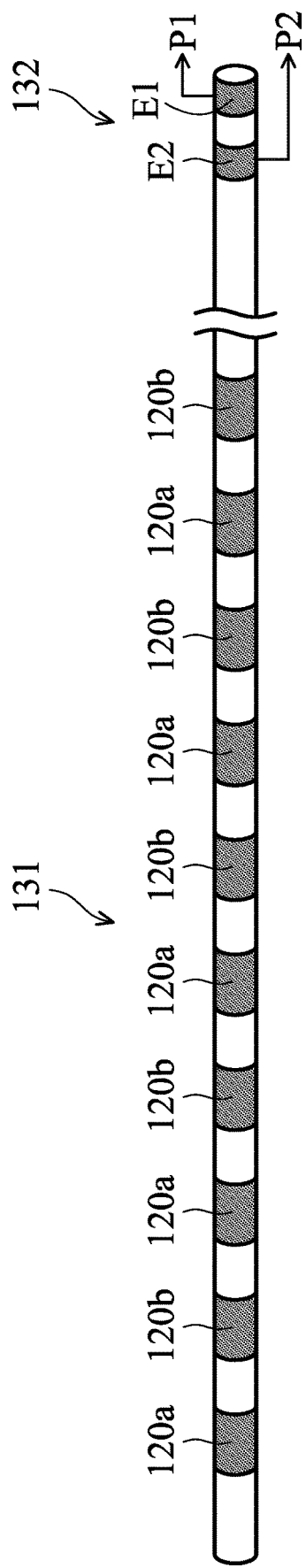
FIG. 4A is a schematic diagram showing a lead connected to an electrical stimulation device according to an embodiment of the present invention.
Figure 4B:
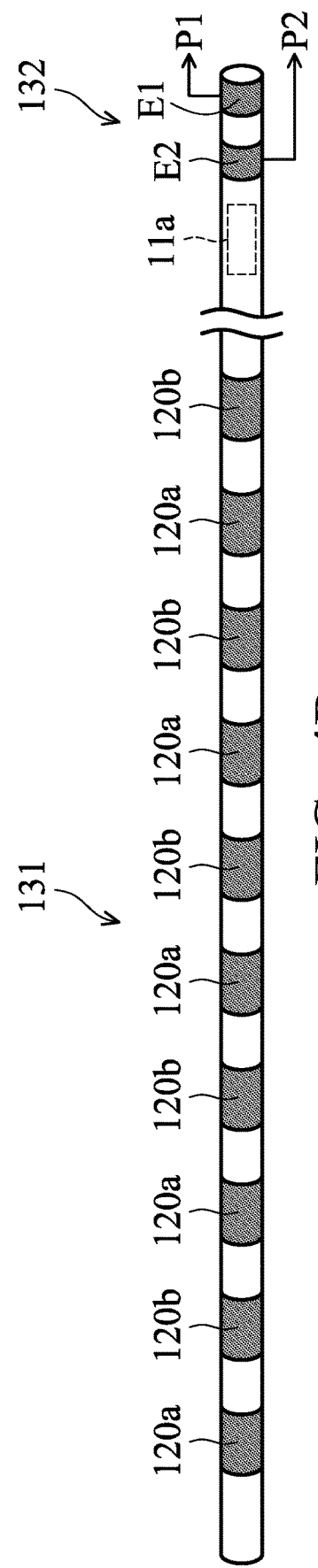
FIG. 4B is a schematic diagram showing a lead connected to an electrical stimulation device according to another embodiment of the present invention.

Referring to FIG. 4A, the electrodes can be divided into the working electrodes 120a and the reference electrodes 120b according to the types of the electrical signals received by the electrodes, and the electrodes are disposed on the distal end 131. In the embodiment, the working electrodes 120a and the reference electrodes 120b are disposed in an interlaced configuration. In an embodiment, the number of working electrodes 120a is equal to the number of reference electrodes 120b. In another embodiment, the number of working electrodes 120a is not equal to the number of reference electrodes 120b. At the proximal end 132, there are two additional electrodes E1 and E2 which directly contact a working-electrode contact P1 (shown in FIG. 5) and a reference-electrode contact P2 (shown in FIG. 5) of the electrical stimulation generation circuit. Moreover, the electrodes E1 and E2 are electrically connected to the working electrodes 120a and the reference electrodes 120b through wires, respectively. For example, the electrode E1 is electrically connected to the working-electrode contact P1 of the electrical stimulation generation circuit and further electrically connected to each working electrode 120a to transmit an electrical signal; the electrode E2 is electrically connected to the reference-electrode contact P2 of the electrical stimulation generation circuit and further electrically connected to each reference electrode 120b to transmit/conduct a reference electrical signal. In FIG. 1, the electrical stimulation generation circuit and the power management circuit are disposed in the electrical stimulation device 11. In another embodiment, as shown in FIG. 4B, the electrical stimulation generation circuit and the power management circuit in the electrical stimulation device may be integrated on a flexible circuit board 11a and disposed in the chamber of the lead 13, so that the electrical stimulation devices and the lead are integrated into a single device without the need for the housing.

Figure 5:
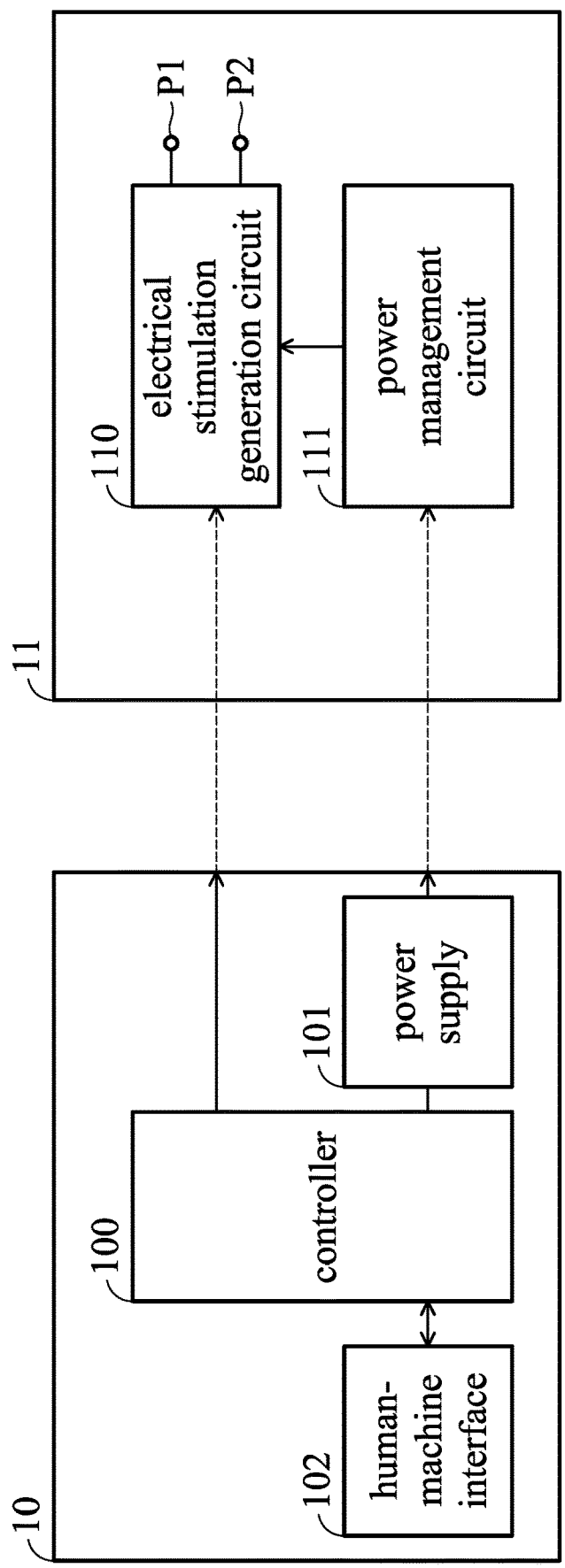
FIG. 5 shows an external control device, an electrical stimulation generation circuit, and a power management circuit according to an embodiment of the present invention.

FIG. 5 shows the external control device 10 and the electrical stimulation generation circuit 110 and the power management circuit in the electrical stimulation device 11 according to an exemplary embodiment of the present invention. Referring to FIG. 5, the external control device 10 comprises a controller 100, a power supply 101, and a human-machine interface 102. The external control device 10 is outside the body of the patient 19 (shown in FIG. 1) and mainly performs the transmission/reception of the signals and energy with the electrical stimulation device 11 implanted in the patient 19 through a wired or wireless communication to charge and control the electrical stimulation device 11. In detail, the controller 100 controls the power supply 101 to transmit energy to the electrical stimulation device 11 through an induced coil or wire for charging. The controller 100 may also generate a control signal and transmit the control signal to control the electrical stimulation generation circuit 110 through a wireless communication (such as a near field and/or Bluetooth communication protocol). The human-machine interface 102 may comprise a keyboard, a mouse, a touch panel, a liquid crystal display, a physical button, or a combination thereof. The user or medical staff can input instructions through the man-machine interface 102, so that the controller 100 can determine the charging parameters of the power supply 101 according to the input parameters. The charging parameters include the amount of the charging current, the amount of the charging voltage, and/or the length of the charging time. The power supply 101 provides power according to the determined charging parameters. After receiving the power from the power supply 101, the power management circuit 111 generates at least a DC (direct-current) voltage to the electrical stimulation generation circuit 110. In addition, the controller 100 may also control the electrical stimulation device 11 according to the input parameters to generate at least one corresponding electrical signal, such as the electrical signal received by the working electrodes. In the embodiment, the electrical stimulation device 11 is an implantable electrical stimulation device that is implanted in the patient's body to generate electrical signals to the leads. Moreover, the electrical stimulation device 11 may also be an external trial stimulator for test. After the lead 13 is implanted in the human body and before the electrical stimulation device is implanted in the human body, the trial stimulator may transmit electrical signals to confirm whether the function of the lead 13 is normal and whether the implanted position of the lead 13 is appropriate. In this case, the, the trial stimulator is not implanted in the human body.

Figure 6:
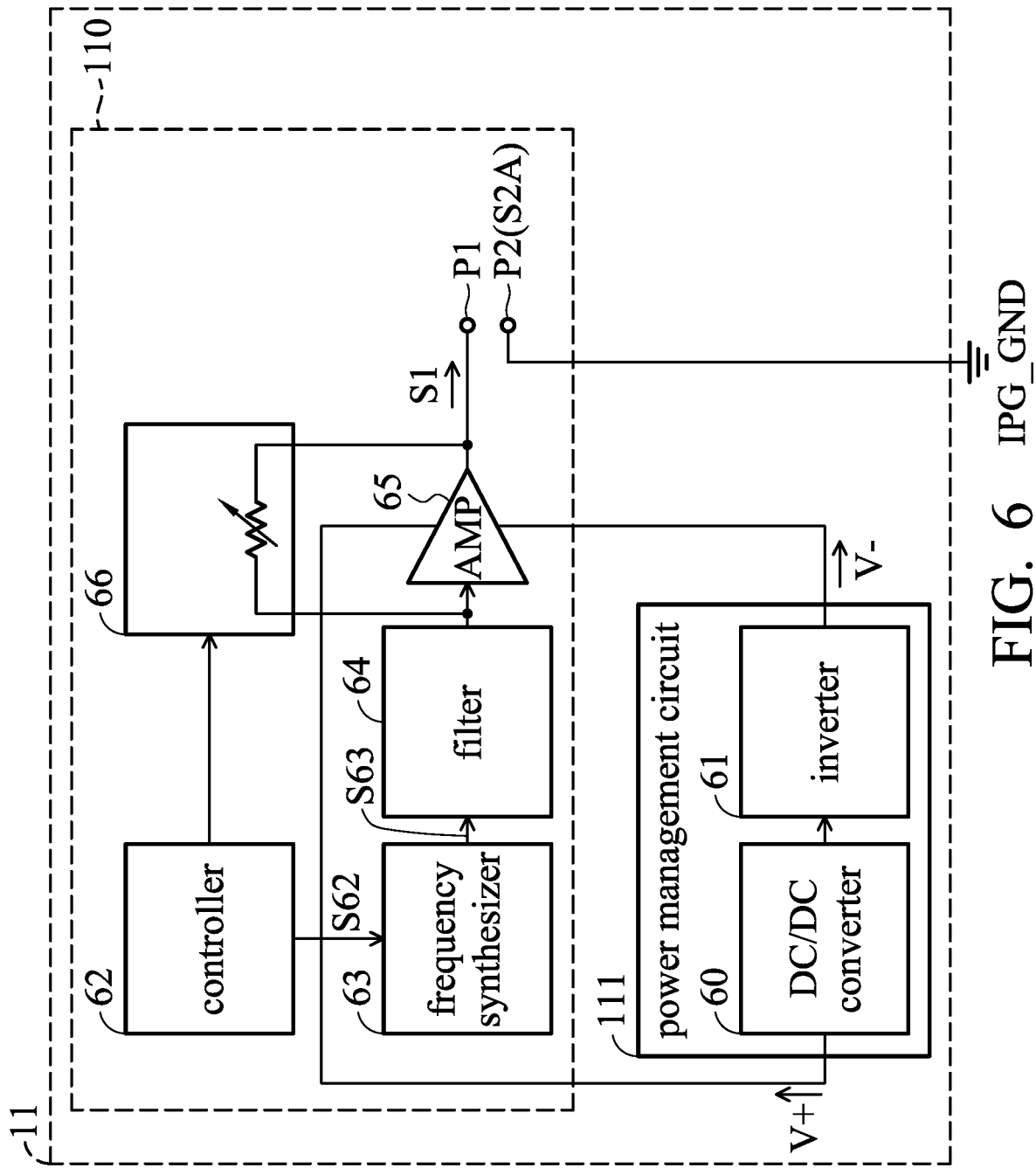
FIG. 6 shows an electrical stimulation generation circuit and a power management circuit according to an embodiment of the present invention.

FIG. 6 shows the electrical stimulation device 11 according to an exemplary embodiment of the present invention. The electrical stimulation device 11 comprises an electrical stimulation generation circuit 110 and a power management circuit 111. Referring to FIG. 6, the electrical stimulation generation circuit 110 comprises a controller 62, a frequency synthesizer 63, a filter 64, an amplifier (AMP) 65, and a variable resistor 66. The electrical stimulation generation circuit 110 may further comprises a working-electrode contact P1 and a reference-electrode contact P2. The working-electrode contact P1 is electrically connected to the working electrodes (such as the working electrodes 120a shown in FIG. 4A) through the lead 13 (shown in FIG. 1), and the reference-electrode contact P2 is electrically connected to the reference electrodes (such as the reference electrodes 120b shown in FIG. 4A) through the lead 13. The power management circuit 111 comprises a DC-DC converter (DC/DC converter) 60 and an inverter 61. The DC-DC converter 60 receives the DC power provided by the power supply 101 through wired or wireless means and changes the voltage level of the received DC power to generate a positive voltage V+. The inverter 61 inverses the positive voltage V+ or another positive voltage generated by the DC-DC converter 60 to generate a negative voltage V−. The positive voltage V+ and the negative voltage V− generated by the power management circuit 111 are used to supply power to the components or devices in the electrical stimulation generation circuit 110. The range of the supplied power may be, for example, ±0V~±30V. The preferred range of the supplied power may be ±0V~±20V. In FIG. 6, the power management circuit 111 providing the positive voltage V+ and the negative voltage V− to the amplifier 65 (that is, the positive voltage V+ and the negative voltage V− serve as its operating power) is given as an example. The controller 62 may generate a control signal S62 according to electrical stimulation parameters to control the frequency synthesizer 63. In this embodiment, the electrical stimulation parameters may be predetermined parameters stored in the controller 62 or may be set by the external control device 10 through wired or wireless means. The frequency synthesizer 63 receives the control signal S62 and generates a frequency signal S63 according to the control signal S62. In the embodiment, the frequency signal S63 is a high frequency signal comprising a plurality of AC (alternating-current) pulses. For example, the frequency signal S63 may be a high frequency signal comprising sine waves, square waves, or a triangular waves. In an embodiment, the frequency synthesizer 63 may be integrated in the controller 62; that is, the electrical stimulation generation circuit 110 comprises the controller 62, the filter 64, the amplifier 65, and the variable resistor 65, and the signal generated by the controller 62 is the frequency signal S63.

Referring to FIG. 6, the amplifier 65 is powered by the positive voltage V+ and the negative voltage V−. The filter 64 is coupled between the frequency synthesizer 63 and the amplifier 65 to filter out the low-frequency component of the frequency signal S63. The amplifier 65 is coupled to the frequency synthesizer 63 through the filter 64 to receive the frequency signal S63 which has been filtered out of the low-frequency component and kept the high-frequency component. The variable resistor 66 is coupled between the input terminal and the output terminal of the amplifier 65. The controller 62 adjusts the resistance value of the variable resistor 66 according to the electrical stimulation parameter(s), thereby changing the gain of the amplifier 65. Therefore, the amplifier 65 generates the electrical signal S1 according to the frequency of the frequency signal S63 and the resistance value of the variable resistor 66 and provides the electrical signal S1 to the working-electrode contact P1. In detail, the frequency of the electrical signal S1 is determined by the frequency signal S63, and the voltage value of the electrical signal S2 is determined by the gain of the amplifier 65 affected by the resistance value of the variable resistor 66. In the embodiment, the reference-electrode contact P2 is directly electrically connected to the ground IPG_GND of the electrical stimulation device 11, wherein the voltage of the ground IPG_GND is, for example, 0V. Therefore, the electrical signal S2A generated at the reference-electrode contact P2 by the electrical stimulation generation circuit 110 is a DC voltage signal of 0V (volt).

Figure 7:
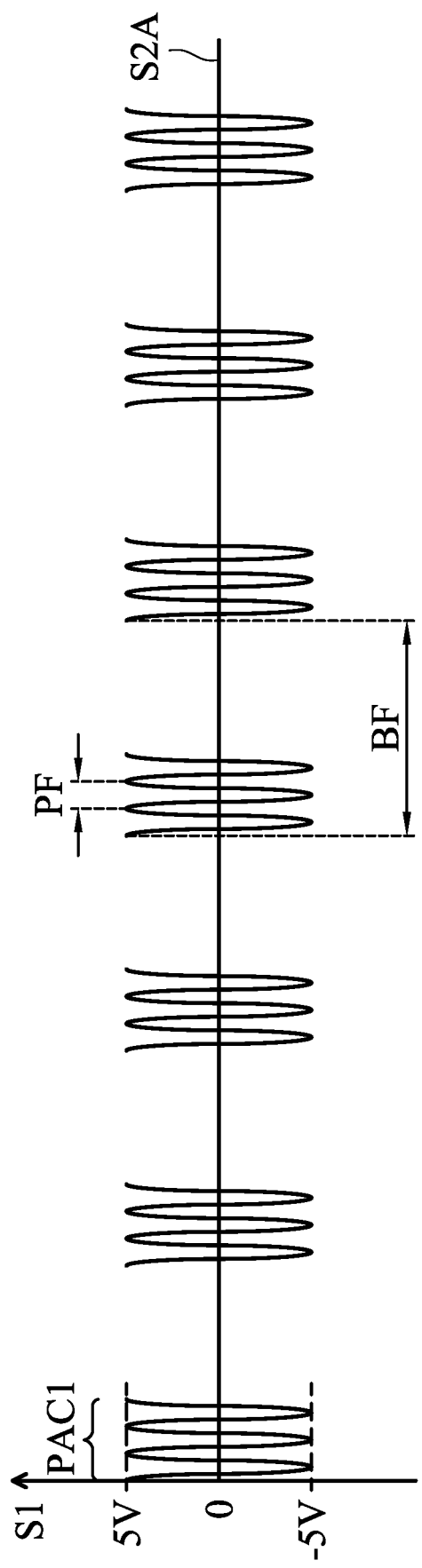
FIG. 7 shows waveforms of electrical signals according to an embodiment of the present invention.

Referring to FIG. 7, in the embodiment of FIG. 6, the electrical signal S1 comprises a plurality of AC pulses PAC1 according to the frequency signal S63. In an embodiment, the pulse frequency PF of the AC pulses PAC1 is in a range of 100 KHz~1000 KHz. The AC pulses PAC1 are generated intermittently. In other words, the AC pulses PAC1 are grouped into a plurality of trains, and there is a time interval between every two pulse trains. In an embodiment, the burst frequency BF of the AC pulses PAC1 is in the range of 1 Hz~100 Hz, preferably in the range of 1 Hz~10 Hz. The duration of each train of AC pulses PAC1 is in the range of 1 ms~250 ms, preferably in the range of 10 ms~100 ms. In addition, according to the gain of the amplifier 65, the peaks of the AC pulses PAC1 are at, for example, +5V, and the valleys thereof are at, for example, −5V. The voltage level of the electrical signal S2A is maintained at 0V and thus the voltage difference between the working electrodes and the reference electrodes of the lead 13 is 5V.

Figure 8:
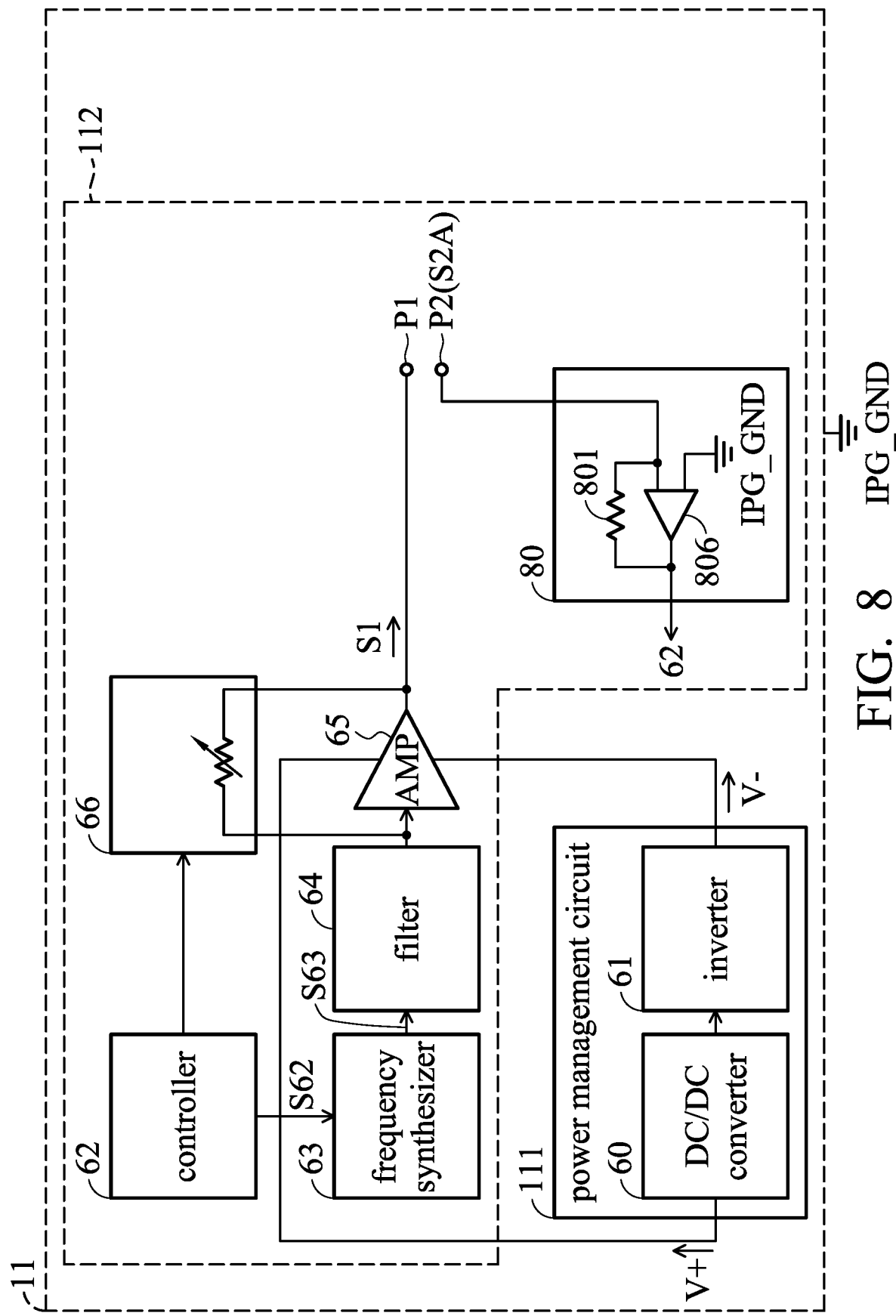
FIG. 8 shows an electrical stimulation generation circuit and a power management circuit according to another embodiment of the present invention.

FIG. 8 shows an electrical stimulation generation circuit 112 and the power management circuit 111 according to an exemplary embodiment of the present invention. In FIGS. 6 and 8, the same elements are represented by the same reference signs. The power management circuit 111 in the embodiment of FIG. 8 is the same as the power management circuit 111 in the embodiment of FIG. 6, and, thus, the description thereof is omitted here. In addition, the electrical stimulation generation circuit 112 of the embodiment of FIG. 8 is similar to the electrical stimulation generation circuit 110 of the embodiment of FIG. 6, and the same elements and circuits refer to the above description of the embodiment of FIG. 6, and, thus, the related description is omitted here. The difference between the embodiment of FIG. 8 and the embodiment of FIG. 6 is that the electrical stimulation generation circuit 112 of the embodiment of FIG. 8 further comprises a current sensor 80. Referring to FIG. 8, the current sensor 80 comprises an operational amplifier 806 and a resistor 801. An input terminal of the operational amplifier 806 is coupled to the reference-electrode contact P2, the other input terminal thereof is coupled to the ground IPG_GND, and an output terminal thereof is coupled to the controller 62. One terminal of the resistor 801 is coupled to the reference-electrode contact P2, and the other terminal thereof is coupled to the output terminal of the operational amplifier 806. When the lead 13 (shown in FIG. 1) is implanted in the human body to form a loop circuit between the working-electrode contact P1 and the reference-electrode contact P2, the current sensor 80 can detect the current of the loop circuit. The detected current can be used to correct the electrical stimulation parameters or used as an electrical stimulation parameter for the controller 62 to generate the control signal S62 and control the variable resistor 66. According to the circuit structure of the current sensor 80, the reference-electrode contact P2 is coupled to the ground IPG_GND through the operational amplifier 806, so that the reference-electrode contact P2 is virtual grounded, and the voltage level of the electrical signal S2A is maintained at 0V, as shown in FIG. 7. Since the paths and elements for generating the electrical signal S1 in the embodiment of FIG. 8 are similar to those in the embodiment of FIG. 6, the electrical signal S1 also comprises AC pulses PAC1 which are presented intermittently, as shown in FIG. 7.

Figure 9:
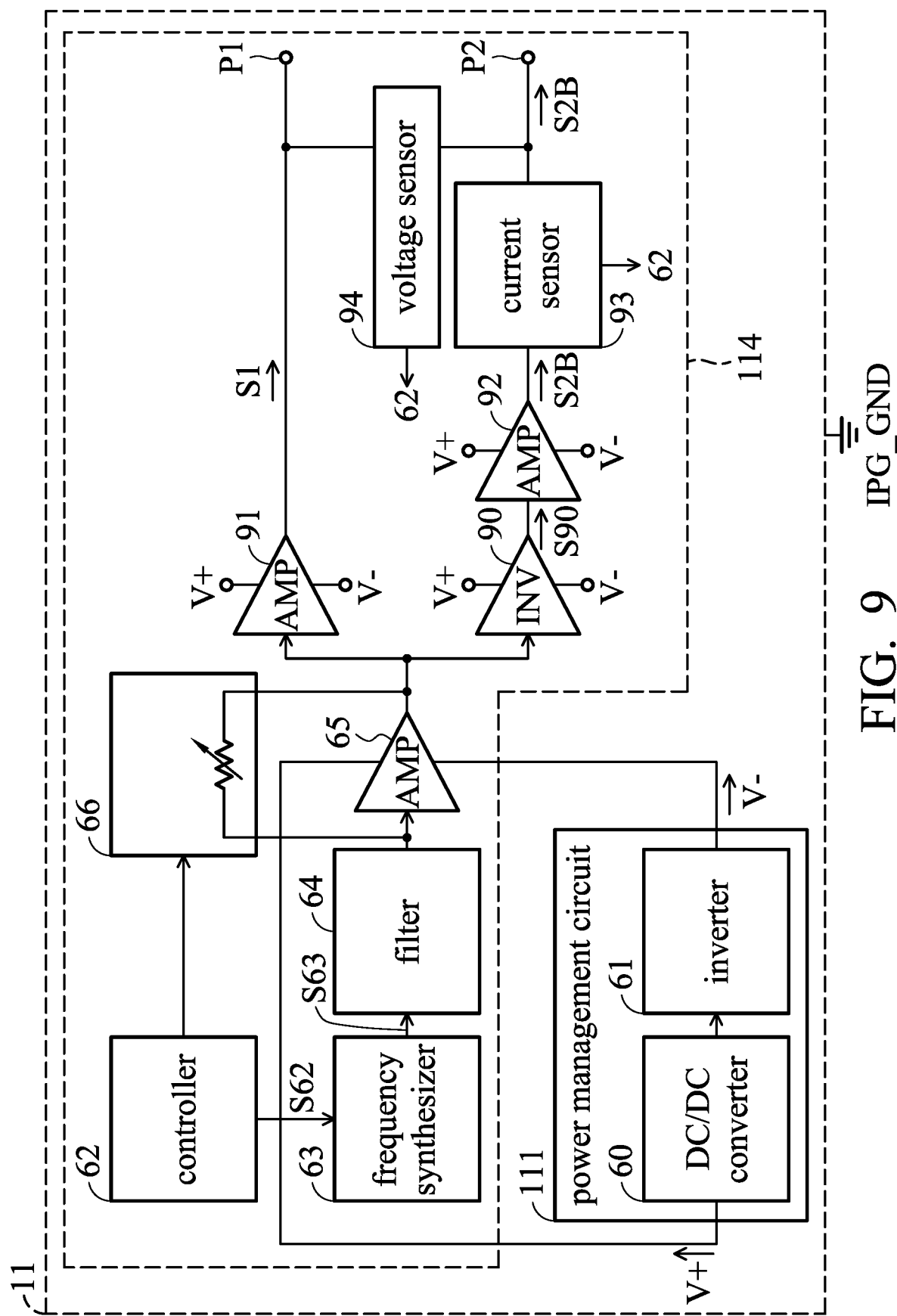
FIG. 9 shows an electrical stimulation generation circuit and a power management circuit according to another embodiment of the present invention.

FIG. 9 shows an electrical stimulation generating circuit 114 and the power management circuit 111 according to another exemplary embodiment of the present invention. In FIGS. 6 and 9, the same elements are denoted by the same reference signs. The power management circuit 111 in the embodiment of FIG. 9 is the same as the power management circuit 111 in the embodiment of FIG. 6, and, thus, the description thereof is omitted here. In addition, the electrical stimulation generation circuit 114 of the embodiment of FIG. 9 is similar to the electrical stimulation generation circuit 110 of the embodiment of FIG. 6, and the same elements and circuits refer to the above description of the embodiment of FIG. 6, and, thus, the related description is omitted here. The difference between the embodiment of FIG. 9 and the embodiment of FIG. 6 is that the electrical stimulation generation circuit 114 of the embodiment of FIG. 9 further comprises an inverter (INV) 90, amplifiers (AMP) 91 and 92, a current sensor 93, and a voltage sensor 94. The power management circuit 111 also provides the positive voltage V+ and the negative voltage V− to the inverter 90, the amplifiers 91 and 92, the current sensor 93, and the voltage sensor 94 to power them. In FIG. 9, the power management circuit 111 providing the positive voltages V+ and the negative voltages V− to the inverter 90 and the amplifiers 91 and 92 is given as an example. Referring to FIG. 9, the amplifier 91 is coupled to the output terminal of the amplifier 65. The amplifiers 65 and 91 which are coupled in series receive the frequency signal S63, which has been filtered out of the low-frequency component and kept the high-frequency component, and perform an amplification operation on the received frequency signal to generate the electrical signal S1. The electrical signal S1 is transmitted to the working-electrode contact P1. The input terminal of the inverter 90 is coupled to the output terminal of the amplifier 65. The input terminal of the amplifier 92 is coupled to the output terminal of the inverter 90. The current sensor 93 is coupled between the output terminal of the amplifier 92 and the reference-electrode contact P2. The inverter 90 receives the frequency signal S63 which has been filtered out of the low-frequency component and amplified by the amplifier 65 and then inverts it to generate an inverted frequency signal S90. After that, the amplifier 92 performs an amplification operation on the inverted frequency signal S90 to generate an electrical signal S2B and provides the electrical signal S2B to the reference-electrode contact P2.

Figure 10:
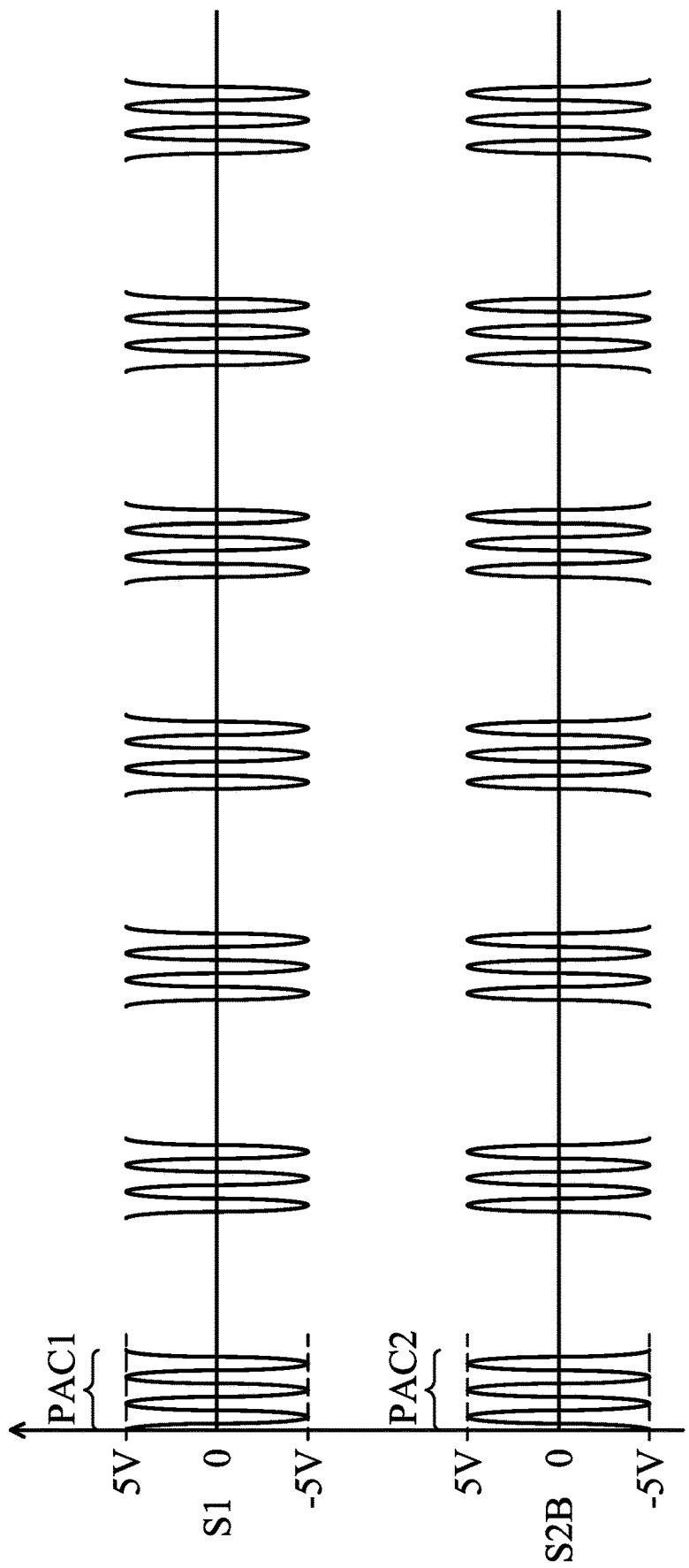
FIG. 10 shows waveforms of electrical signals according to another embodiment of the present invention.

According to the embodiment of FIG. 9, after the amplifier 65, there is one amplifier 91 in the path which is provided to generate the electrical signal S1, and there is one amplifier 92 and one inverter 90 in the path which is provided to generate the electrical signal S2B. As described above, since the frequency signal S63 is a high-frequency signal comprising a plurality of AC pulses, the electrical signal S1 generated according to the frequency signal S63 also comprises a plurality of AC pulses PAC1 which are presented intermittently, as shown in FIG. 10. In addition, the electrical signal S2B generated according to the frequency signal S63 similarly comprises a plurality of AC pulses PAC2 which are presented intermittently. Therefore, in the embodiment, both of the electrical signals S1 and S2B are AC signals. It should be noted that, due to the operation of the inverter 90, the AC pulses PAC1 of the electrical signal S1 and the AC pulses PAC2 of the electrical signal S2B are mutually in opposite phases, as shown in FIG. 10. Since the AC pulses PAC1 and the AC pulses PAC2 are mutually in opposite phases, the voltage difference between the working electrodes and the reference electrodes of the lead 13 can reach 10V (doubled the voltage difference of the embodiment shown in FIG. 7). Accordingly, the signal intensity of the electrodes is increased in an equivalent additive and multiplying effect without the need for additional voltage-rising circuits, thereby reducing the cost of the device. In the embodiment of FIG. 9, the amplifiers 91 and 92 may be high output current or voltage amplifiers, so that the loading on the pre-amplifier 65 may be reduced.

In the embodiment of FIG. 9, when the lead is implanted in the human body to form a loop circuit between the working-electrode contact P1 and the reference-electrode contact P2, the current sensor 93 can detect the current of the loop circuit. The voltage sensor 94 is coupled to the working-electrode contact P1 and the reference-electrode contact P2 to detect the voltages on the working-electrode contact P1 and the reference-electrode contact P2, i.e. the voltage of the loop circuit. The detection results of the current sensor 93 and the voltage sensor 94 may be used to modify the electrical stimulation parameters or may serve as an electrical stimulation parameters for the controller 62 to generate the control signal S62 and control the variable resistor 66.

Figure 11:
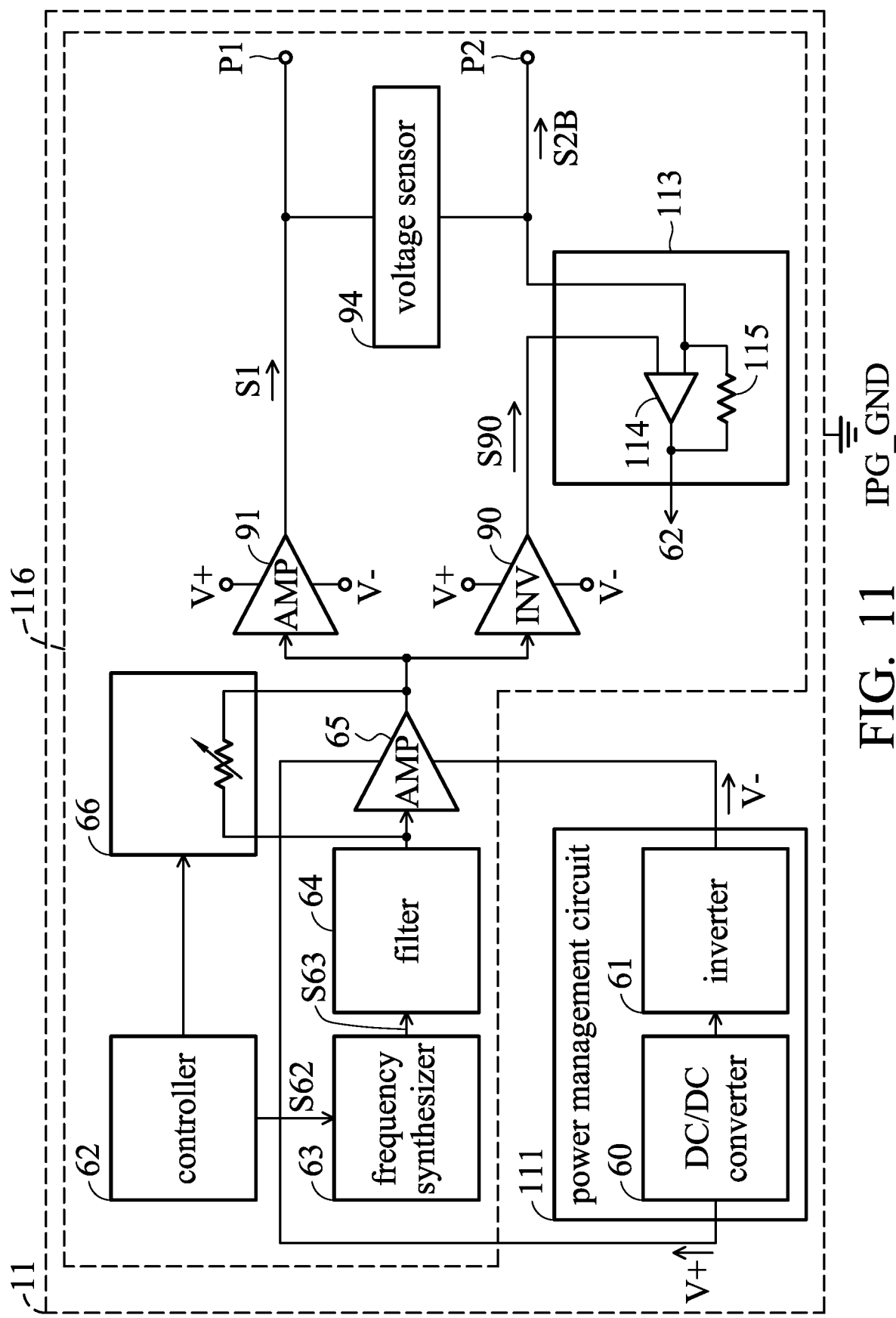
FIG. 11 shows an electrical stimulation generation circuit and a power management circuit according to an embodiment of the present invention.

In another embodiment, the amplifier 92 in the embodiment of FIG. 9 can be implemented by a current sensor. Referring to FIG. 11, a current sensor 113 replaces the current sensor 93 of FIG. 9. The current sensor 113 comprises an operational amplifier 114 and a resistor 115. The first input terminal of the operational amplifier 114 is coupled to the output terminal of the inverter 90 to receive the inverted frequency signal S90, the second input terminal thereof is coupled to the reference-electrode contact P2, and the output terminal thereof is coupled to the controller 62. The operational amplifier 114 and the resistor 115 form an amplifier for amplifying the inverted frequency signal S90 to generate an electrical signal S2B. In addition, the circuit formed by the operational amplifier 114 and the resistor 115 can also sense the current of the loop circuit which is formed between the working-electrode contact P1 and the reference-electrode contact P2 when the lead is implanted into the human body. The signal generated at the output terminal of the operational amplifier 114 indicates the magnitude of the current at the reference-electrode contact P2. The detection result of the current sensor 113 may be transferred back to the controller 62 and be used to modify the electrical stimulation parameters or as an electrical stimulation parameter for the controller 62 to generate the control signal S62 and control the variable resistor 66.

Figure 12:
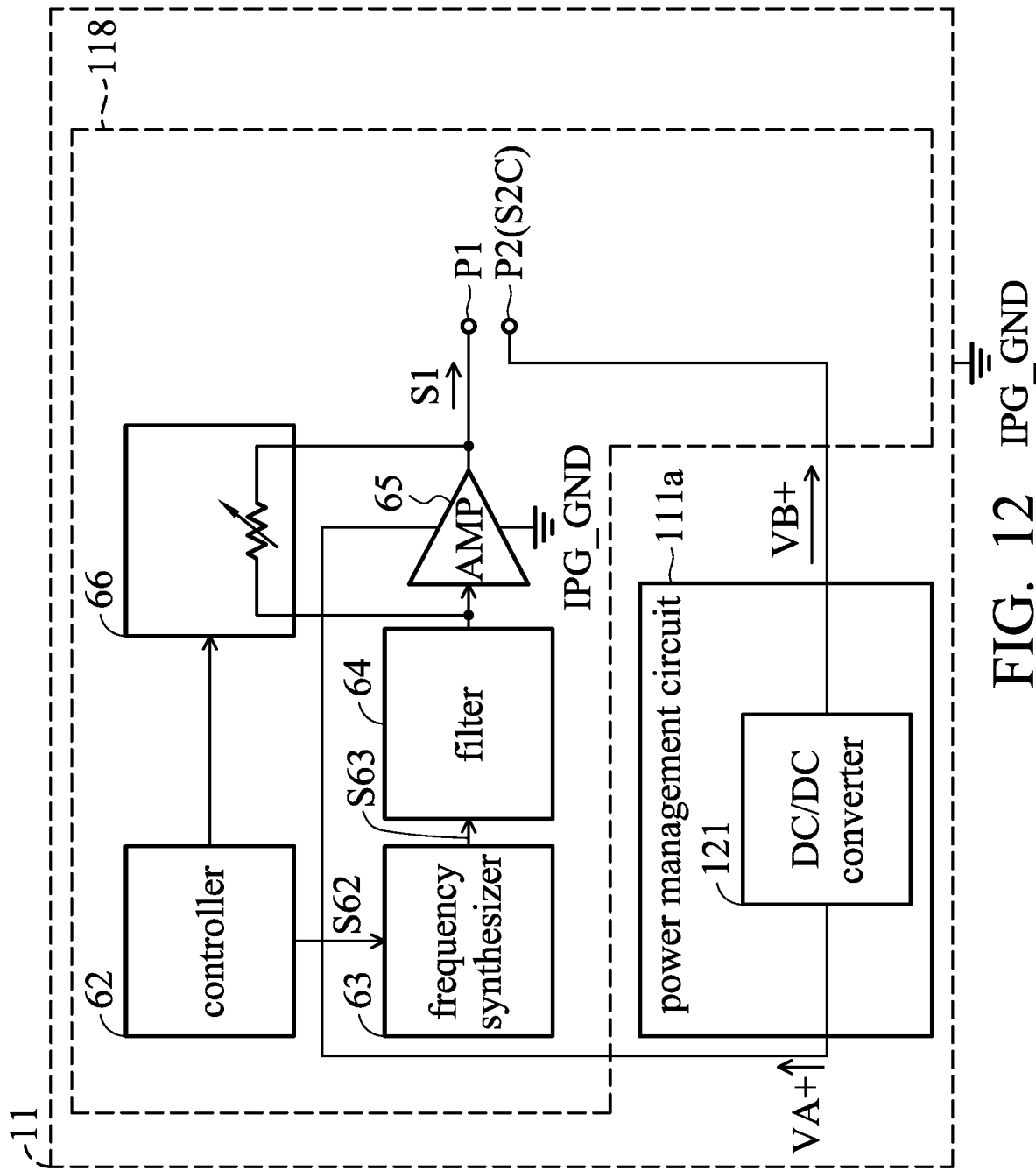
FIG. 12 shows an electrical stimulation generation circuit and a power management circuit according to another embodiment of the present invention.

FIG. 12 shows an electrical stimulation generation circuit 118 and a power management circuit 111a according to another embodiment of the present invention. In FIGS. 6 and 12, the same elements are denoted by the same reference signs. Compared with the embodiment of FIG. 6, the power management circuit 111a in the embodiment of FIG. 12 comprises only a DC-DC converter (DC/DC converter) 121 without the inverter 61 shown in FIG. 6. The DC-DC converter 121 receives the DC power provided by the power supply 101 (shown in FIG. 5) through wired or wireless means and changes the voltage level of the received DC power to generate positive voltages VA+ and VB+, which means the first voltage and the second voltage are direct-current voltages with different levels. The positive voltage VA+ generated by the DC-DC converter 121 is used to power elements or devices in the electrical stimulation generation circuit 118. In FIG. 12, the DC-DC converter 121 providing the positive voltage VA+ to the amplifier 65 is provided as an example. In this embodiment, the amplifier 65 is further coupled to the ground IPG_GND as another operating power. In addition, the electric stimulation generation circuit 118 of the embodiment of FIG. 12 is similar to the electric stimulation generation circuit 110 of the embodiment of FIG. 6, and the same elements and circuits will refer to the above description about the embodiment of FIG. 6, thus, the related description will be omitted here. Compared with the embodiment of FIG. 6, the electrical stimulation generation circuit 118 in the embodiment of FIG. 12 receives the voltage VB+ and provides the voltage VB+ to the reference-electrode contact P2. Therefore, it can be known that the electrical signal S2C generated the reference-electrode contact P2 by the electrical stimulation generation circuit 110 is a DC voltage signal with a positive voltage level.

Figure 13:
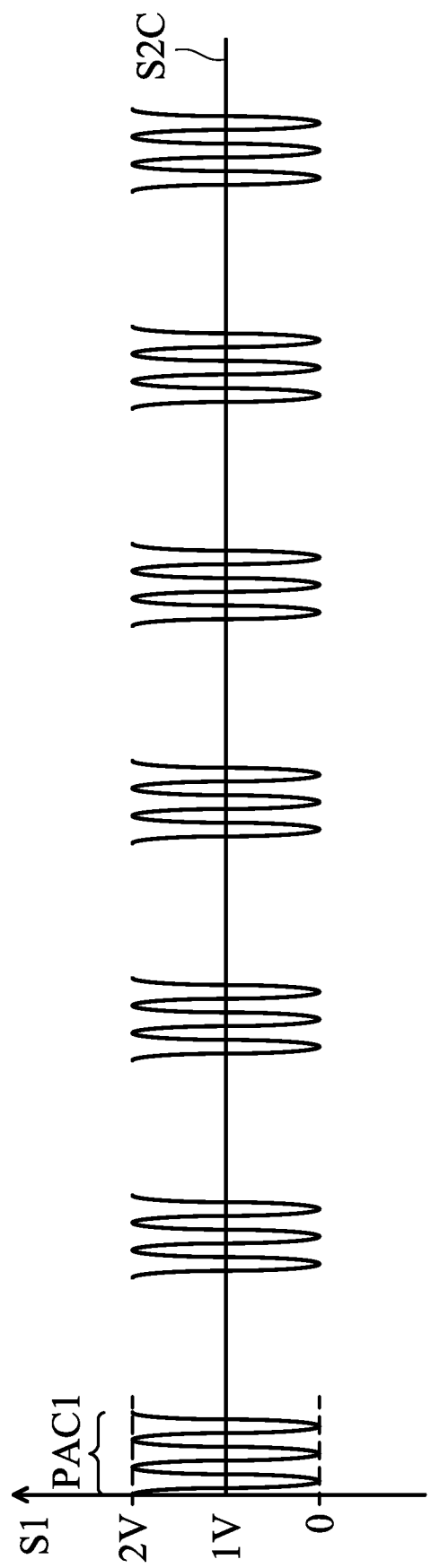
FIG. 13 shows waveforms of electrical signals according to an embodiment of the present invention.

Referring to FIG. 13, in the embodiment of FIG. 12, the electrical signal S1 comprises a plurality of AC pulses PAC1 according to the frequency signal S63, and the AC pulses PAC1 are generated intermittently. In addition, according to the gain of the amplifier 65, the peaks and valleys of the AC pulses PAC1 can both be at positive voltage level, for example, the peaks are at +2V, and the valleys thereof are at, for example, 0V. The voltage level of the electrical signal S2C is maintained at the level of the voltage VB+, for example, 1V.

According to the above embodiments, the working electrodes 120a of the lead 13 receive the AC electrical signal S1, and the reference electrodes 120b of the lead receive the DC signal S2A or S2C with the fixed level or the AC signal S2B which is inverted to the electrical signal S1. When the lead 13 is implanted in the body of the patient for electrical stimulation, the working electrodes 120a and the reference electrodes 120b form an electrical loop circuit via the patient serving as a medium to transmit the electrical stimulation signal to the body (the signal intensity between the two electrodes 120a and 120b is preferably between −20V and +20V; the current is between 2 mA and 50 mA; and the duration is between 1 ms and 250 ms, preferably between 10 ms and 100 ms) to perform electrical stimulation on the target region. The implantation position of the electrodes of the lead 13 is quite close to the target region 15. For example, the distance between the target region 15 and the nearest electrode 120 is less than 10 mm. In addition, an electric field is also generated between each set of the working electrode 120a and the reference electrode 120b to cover the target region. Since the electrical stimulation signal is an intermittent AC-pulse signal, the formed electric field is an AC intermittent pulsed electric field. The strength of the electric field is between 100V/m and 2000V/m. The strength of the electric field is obtained by simulating the strength of the electric field using a finite element method (FEM) in a software manner. For example, the analysis software is an AC/DC module of COMSOL Multiphysics (MI, USA).

Accordingly, the brain, spinal cord, dorsal root nerve or spinal nerve in the target range 15 can be stimulated only by providing electrical signals to the working electrodes and the reference electrodes, so as to block or inhibit the signal between the neurons and thus relieve pain in the patient 19 (for example, to block or inhibit nerve conduction in C-fibers for 2 hours to 7 days through one duration time, i.e. 1~30 minutes per treatment, 1~5 treatments per day) or to treat specific diseases. The medical personnel operating the electrical stimulation system 1 do not need to perform the conventional electrode polarity selection and switching operations. Thus, it is convenience to medical personnel, and the operating and treatment time is also decreased. In addition, since the conventional electrode polarity selection and switching operations do not need to be performed any more, no conventional switch array is required in the electrical stimulation device 11 of the present invention, thereby reducing the volume and component cost of the electrical stimulation device 11. Furthermore, since at least one electrical stimulation signal is an AC signal, the working electrodes and the reference electrodes can serve as a reference electrode for each other, so there is no need to provide an additional reference electrode on the lead or on the extension.

Figure 14:
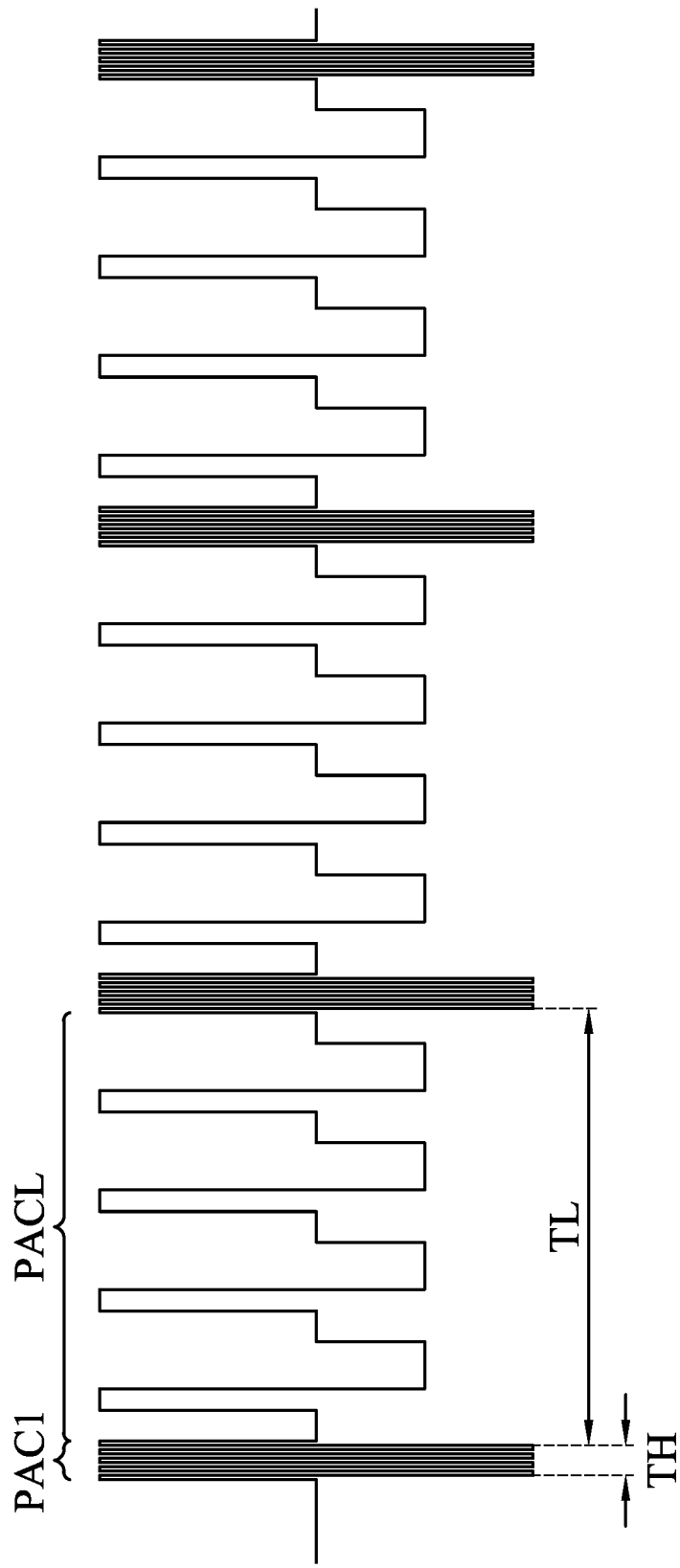
FIG. 14 shows waveforms of electrical signals according to another embodiment of the present invention.

In the above embodiments, the electrical signal S1 comprises a plurality of AC pulses PAC1 which are generated intermittently. Here, the AC pulses PAC1 are square waves. Of course, the AC pulses PAC1 may also be sine waves. In other embodiments, the controller 62 may control the frequency synthesizer 63 to generate AC pulses with different frequencies, such that there are AC pulses PACL in the interval TL between every two bursts of AC pulses PAC1, and the frequency of the AC pulses PACL is different from the frequency of the AC pluses PAC1. Referring to FIG. 14, the electrical signal S1 comprises a burst of AC pulses PAC1 in each burst duration TH, and each burst comprises a plurality of pulses. There are a plurality of AC pulses PACL in each interval TL, and the duration time of the AC pulses PACL between two bursts of AC pulses PAC1 is shorter than or equal to the interval TL. In this embodiment, the duration time of the AC pulse PACL is equal to the interval TL. Therefore, the bursts of AC pulse PAC1 and the groups of AC pulses PACL appear alternately in time, that is, the duration TL of one groups of AC pulses PACL does not overlap the duration TH of one burst of AC pulses PAC1. In addition, the pulse frequency of the AC pulses PAC1 (100 kHz~1000 kHz) is greater than the frequency of the AC pulses PACL (0.1 Hz~1 kHz). In this embodiment, the AC pulses PACL with a lower frequency is taken at a frequency of 0.1 Hz to 10 Hz as an example. The low-frequency AC pulses PACL can allow the patient 19 to give a muscle beating response or cover pain or paresthesia of the patient 19 when the electrical stimulation device 11 is implanted, so that whether the position of the lead is implanted correctly can be fed back to the medical personnel through the patient's response, which prevents the implanted position of the electrodes from deviating from the target region 15. It should be noted that the positive-phase signal and the negative-phase signal of the electrical signal S1 must achieve a charge balance in order to reduce the damage to the nerve caused by the electrical stimulation treatment.

According to an embodiment of the present invention, a computer-readable storage medium (such as, a flash memory or a read-only memory) stores one or more instructions. The computer-readable storage medium is coupled to the external control device 10 or the controller 100 of the external control device 10. When the controller 100 controls the electrical stimulation device 11 or transmits the instructions to the electrical stimulation device 11 in a wired or wireless manner, the electrical stimulation device 11 executes these instructions and performs the operation of any of the above embodiments to generate the electrical signals S1 and S2A/S2B/S2C to electrically stimulate the target region.

Figure 15:
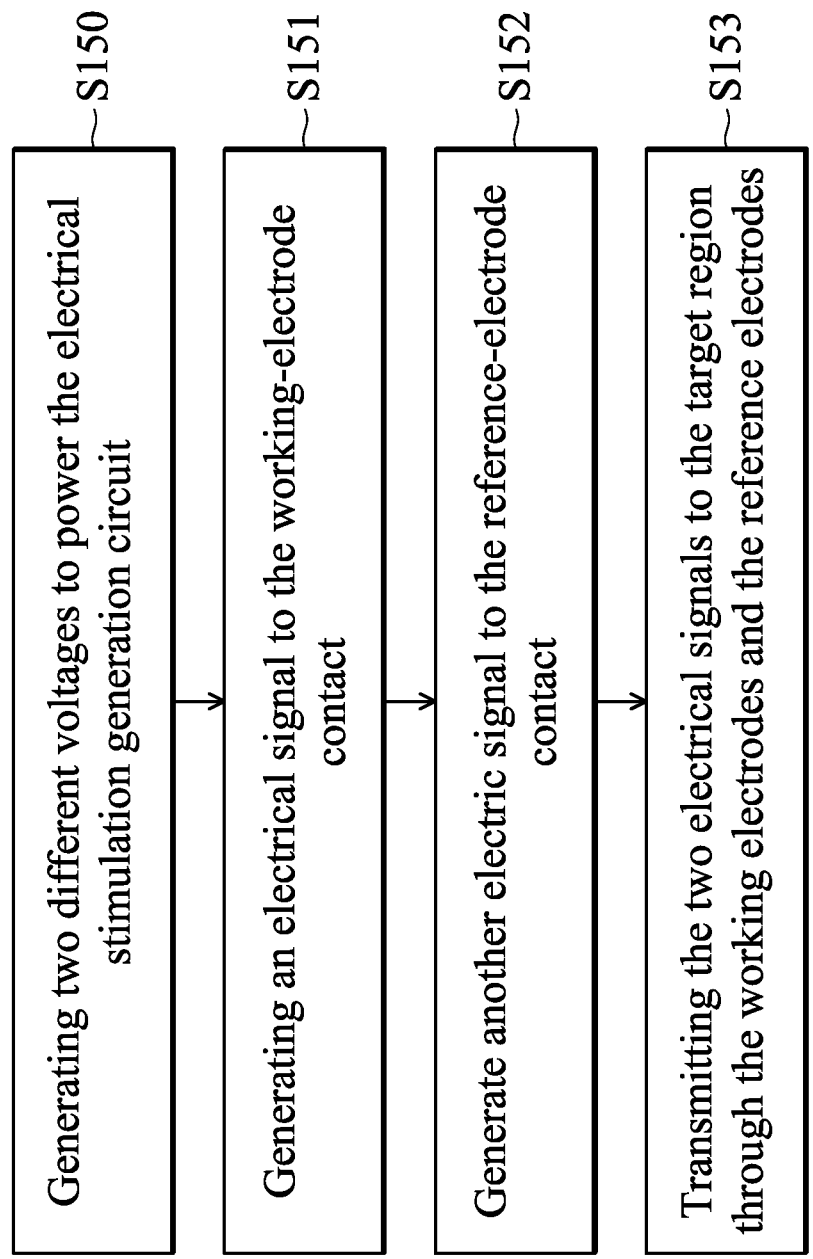
FIG. 15 shows a flow chart of a method of generating electrical signals according to an embodiment of the present invention.

FIG. 15 is a diagram illustrating a method of generating electric signals according to an embodiment of the present invention. Referring to FIG. 15, the method 150 of generating electrical signals may be implemented by the electrical stimulation device 11 in any one of the embodiments of FIGS. 5-6, 8-10, and 11-12. When the electrical stimulation device 11 performs the method 150, two different voltages are generated by the power management circuit 111 in the electrical stimulation device 11 to power the electrical stimulation generation circuit 110, 112, 114, 116, or 118 (step S150). The powered electrical stimulation circuit operates to generate an electrical signal to the working-electrode contact P1 (step S151), such as the electrical signal S1 in FIG. 7, 10, 13, or 4. According to an embodiment of the invention, the electrical signal S1 comprises a plurality of AC pulses. The powered electric stimulation generation circuit operates to further generate another electric signal to the reference-electrode contact P2 (step S152). According to an embodiment of the invention, the electrical signal generated at the reference-electrode contact P2 is a signal with a fixed voltage level, such as, the electrical signal S2A with a 0V level in FIG. 7, or the electrical signal S2C with a 1V level in FIG. 13. According to another embodiment of the present invention, the electrical signal generated at the reference-electrode contact P2 comprises has a plurality of AC pulses, and these AC pulses and the AC pulses of the electrical signal S1 are mutually in opposite phases, such as the electrical signal S2B in FIG. 10. The above electrical signals may be generated according to any one of the embodiments shown in FIGS. 5-6, 8-10, and 11-12, and the related descriptions are represented in the foregoing paragraphs and omitted here. After the electrical signals S1 and S2A/S2B/S2C are generated, the electrical stimulation generation circuit transmits the electrical signals S1 and S2A/S2B/S2C to the target region through the working electrodes 120a and the reference electrodes 120b of the lead 13 (shown in FIGS. 4A and 4B) (step S153) to electrically stimulate the target region, thereby blocking or inhibiting the signal between the neurons for slowing down the pain of the patient 19 or treating a specific disease.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). For example, it should be understood that the system, device and method may be realized in software, hardware, firmware, or any combination thereof. Therefore, the scope of the appended claims should be accorded the broadest interpretation so as to encompass all such modifications and similar arrangements.

What is claimed is:

1. An electrical stimulation device comprising:
   a power management circuit generating a first voltage and a second voltage; and
   an electrical stimulation generation circuit, powered by the first voltage and the second voltage, comprising a first contact and a second contact, generating a first electrical signal at the first contact according to the first voltage and the second voltage, and generating a second electrical signal at the second contact,
   wherein the electrical stimulation device is electrically connected to a lead, a working electrode and a reference electrode are disposed on the lead, the first contact is coupled to the working electrode through the lead, and the second contact is coupled to the reference electrode through the lead, and
   wherein the first electrical signal comprises a plurality of first alternating-current (AC) pulses configuring to electrically stimulate a target region of a target object.

2. The electrical stimulation device as claimed in claim 1, wherein the first voltage is a positive voltage, and the second voltage is a negative voltage.

3. The electrical stimulation device as claimed in claim 2, wherein the second contact is coupled to a ground of the electrical stimulation device.

4. The electrical stimulation device as claimed in claim 1, wherein the first voltage and the second voltage are direct-current voltages with different levels.

5. The electrical stimulation device as claimed in claim 1, wherein the second electrical signal is a signal with a fixed voltage level.

6. The electrical stimulation device as claimed in claim 1, wherein the second electrical signal comprises a plurality of second AC pulses, and the plurality of first AC pulses and the plurality of second AC pulses are mutually in opposite phases.

7. The electrical stimulation device as claimed in claim 1, wherein the electrical stimulation generation circuit comprises:
   a controller generating a frequency signal; and
   a first amplifier, powered by the power management circuit, generating the first electrical signal according to the frequency signal.

8. The electrical stimulation device as claimed in claim 7, wherein the electrical stimulation generation circuit further comprises:
- an inverter receiving the frequency signal and generating an inverted frequency signal according to the frequency signal.

9. The electrical stimulation device as claimed in claim 8, wherein the electrical stimulation generation circuit further comprises:
- an operational amplifier comprising a first input terminal receiving the inverted frequency signal, a second input terminal coupled to the second contact, and an output terminal; and
- a resistor coupled to the second input terminal and the output terminal of the operational amplifier.

* * * * *